(12) United States Patent
Akai et al.

(10) Patent No.: US 6,421,078 B1
(45) Date of Patent: Jul. 16, 2002

(54) ELECTRONIC ENDOSCOPE SYSTEM

(75) Inventors: Nobuyuki Akai, Saitama; Kaneo Yajima, Tokyo, both of (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/502,465

(22) Filed: Feb. 11, 2000

(30) Foreign Application Priority Data

Feb. 12, 1999 (JP) .......................................... 11-034116

(51) Int. Cl.$^7$ ................................................. H04N 7/18
(52) U.S. Cl. .............................. 348/65; 348/69; 348/76
(58) Field of Search .............................. 348/65, 68, 69, 348/70, 71, 76, 223, 224, 227; 600/109, 160

(56) References Cited

U.S. PATENT DOCUMENTS 5,333,010 A * 7/1994 Nakamura et al. .......... 348/263
5,339,159 A * 8/1994 Nakamura et al. .......... 348/263

* cited by examiner

Primary Examiner—Vu Le
(74) Attorney, Agent, or Firm—Young & Thompson

(57) ABSTRACT

An electronic endoscope system comprises an electronic endoscope unit equipped with a solid state image pickup element for providing electric signals of an object and a processing unit for processing the electric signals to video signals. During performing black balance adjustment, the processing unit interrupts only vertical transfer signals included in drive signals, vertical and horizontal drive signals, for driving the solid state image pickup element so as to cause the solid state image pickup element to provide electric signals at the same level as electric signals that the solid state image pickup element provides while it is in isolated from ambient light.

3 Claims, 2 Drawing Sheets

ELECTRONIC ENDOSCOPE SYSTEM

BACKGROUND OF THE INVENTION

1. Field of the Invention

This invention relates to an electronic endoscope system.

2. Description of Related Art

Typically, as schematically shown in FIG. 2, an electronic endoscope system comprises an electronic endoscope 101 which is inserted into a human body, a processing unit 102 and a monitor television (not shown). Such an electronic endoscope 101 has an objective lens 104 disposed at a distal end thereof, a solid state image pickup element 105 disposed in a focal position of the objective lens 104 and a light guide 103 which guides light from light source outside the electronic endoscope from one end to another end thereof and directs the light toward the inside of an organ of a human body. The processing unit 102 includes therein an illumination device comprising an illumination lamp 108 and energizing means 109 for the illumination lamp 108, an iris 107 operative to limit the diameter of the bundle of light rays, i.e. the quantity of light, emanating from the illumination lamp 108 or shut off the bundle of light rays emanating from the illumination lamp 108, and a focusing lens 106 operative to focus the light rays passing through the iris 107 at an end of the light guide 103. The light rays emanating from the illumination lamp 108 and focused on the end surface of the light guide 103 are transmitted by the light guide 103 and directed toward an object to illuminate it. Light rays reflected by the object are focused on the solid state image pickup element 105 by the objective lens 106 so as to form an optical image of the object on the solid state image pickup element 105.

The processing unit 102 includes a drive signal generating circuit 112, a black balance adjusting circuit 113, a white balance adjusting circuit 114, a video signal processing circuit 115 and a display control circuit 116 therein. Specifically, the drive signal generating circuit 112 generates a drive signal with which the solid state image pickup element 105 is driven and controlled to photo-electrically convert the optical image thereon into image signals. The image signals provided by the solid state image pickup element 105 are adjusted in black and white balances by the black balance adjusting circuit 113 and the white balance adjusting circuit 114, respectively. The adjusted image signals are subsequently processed for gamma correction etc. by the video signal processing circuit 115 and then converted to television signals Sv through the display control circuit 116 and transmitted to the monitor television to display an image of the object on the screen.

When a black balance adjusting command 18 is entered, an iris drive circuit 110 drives the iris 107 to close. While the iris 107 remains closed, the black balance adjusting circuit 113 is actuated to perform black balance adjustment for a specified period of time. Similarly, when a white balance adjusting command is entered, the iris drive circuit 110 drives the iris 107 to close. While the iris 107 remains closed, the white balance adjusting circuit 114 is actuated to perform black balance adjustment for a specified period of time.

In the electronic endoscope system, it is necessary to isolate the distal end portion, more specifically at least the solid state image pickup element, of the electronic endoscope from ambient light while completely closing the iris so as to prevent illumination light emanating from the lamp from reaching the light guide during performing black balance adjustment of the electronic endoscope 101, which is always troublesome adjustment operation.

SUMMARY OF THE INVENTION

It is therefore an object of the invention to provide an electronic endoscope system which has no necessity of closing an iris so as to shut off illumination light from an endoscope nor necessity of isolating an solid state image pickup element from ambient light during performing black balance adjustment.

The foregoing object of the present invention is accomplished by an electronic endoscope system comprising an electronic endoscope unit equipped with a photoelectric conversion element as an image pickup element for photo-electrically converting light from an object to electric signals and a signal processing unit for processing the electric signals to video signals, the processing unit comprising drive signal generating means for generating vertical and horizontal transfer signals as drive signals with which the photoelectric conversion element is driven, color balance adjusting means for adjusting at least black balance of the photoelectric conversion element, and transfer signal interruption means for interrupting the vertical transfer signals from the photoelectric conversion element and admitting the horizontal transfer signals to the solid state image pickup element so as to cause the photoelectric conversion element to perform horizontal transfer only while the balance adjusting means is actuated.

BRIEF DESCRIPTION OF THE DRAWINGS

The above and other objects and features of the present invention will be understood from the following description of a specific embodiment thereof when considering in conjunction with the accompanying drawings, in which same or similar parts are denoted by the same reference numerals throughout the drawings, and where.

DETAILED DESCRIPTION OF THE SPECIFIC EMBODIMENT

Figure 1:
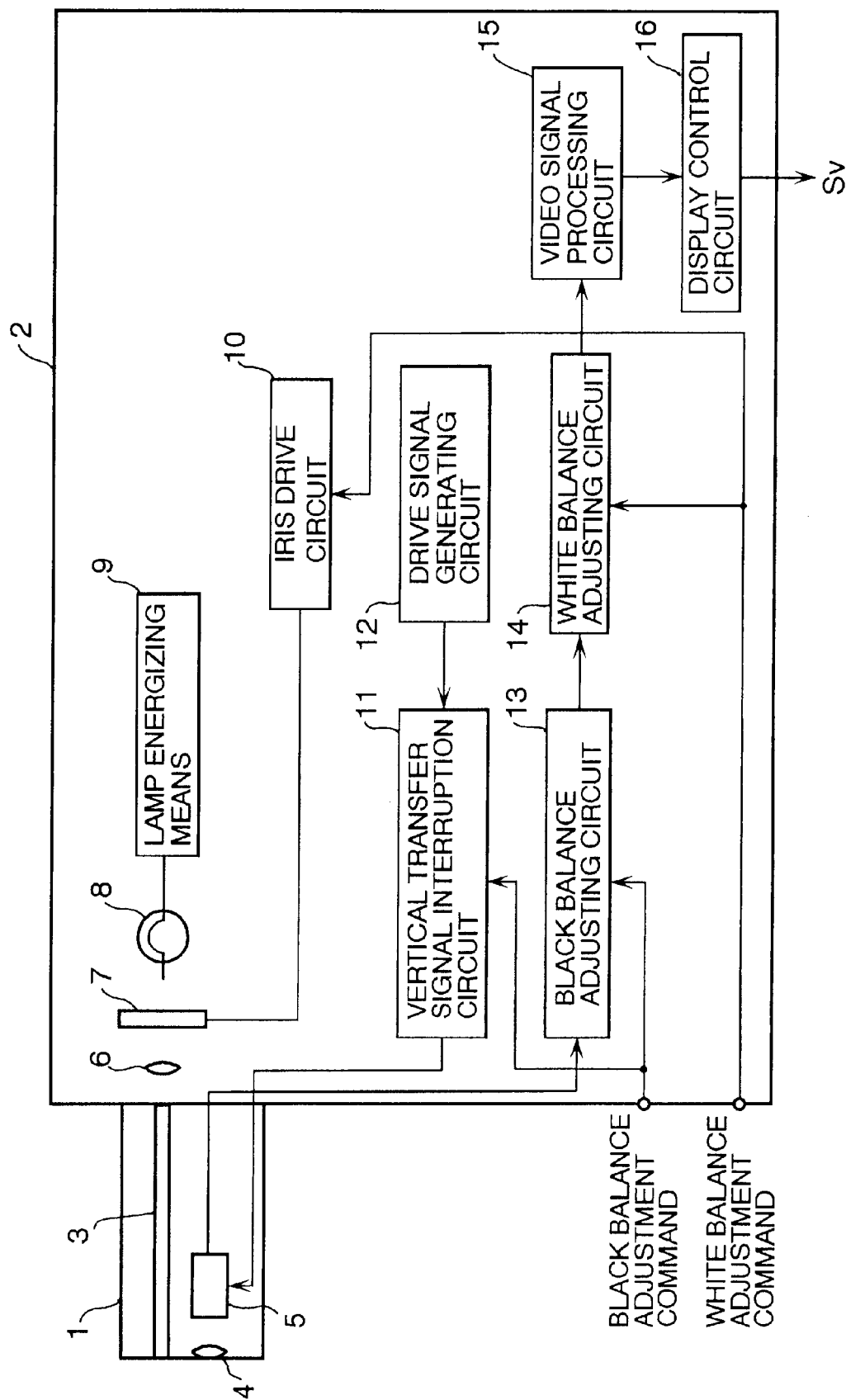
FIG. 1 is a block diagram illustrating an electronic endoscope system in accordance of a preferred embodiment of the present invention.
Figure 2:
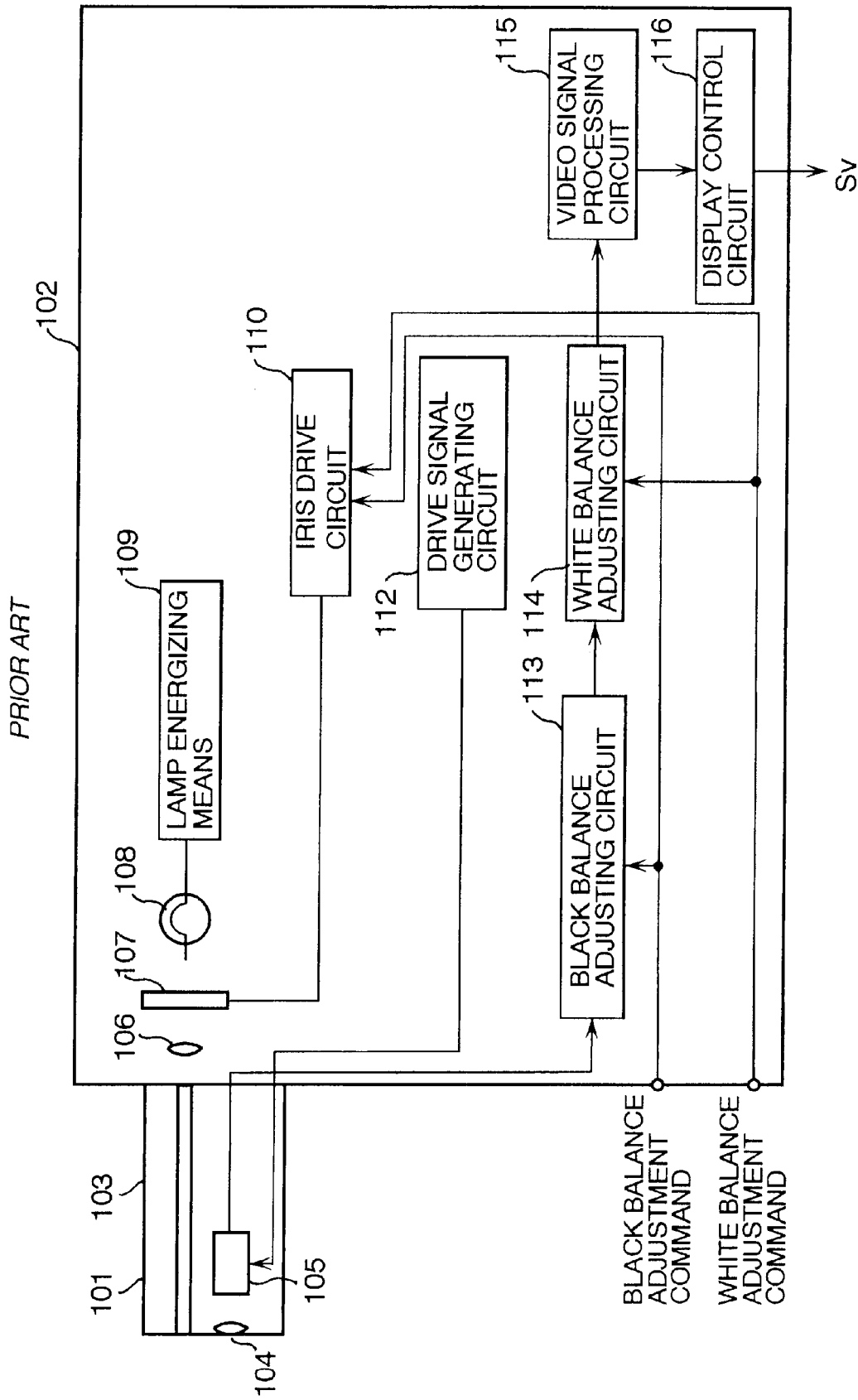
FIG. 2 is a block diagram illustrating a prior art electronic endoscope system.

Referring to FIG. 1 schematically showing an electronic endoscope system according to a preferred embodiment of the invention, the electronic endoscope system comprises an electronic endoscope 1 and a processing unit 2. The electronic endoscope 1 has an objective lens 4 disposed at a distal end thereof, a solid state image pickup element 5 such as a photoelectric conversion element disposed in a focal position of the objective lens 4 and a light guide 3 such as a fiber bundle comprising a number of optical fibers which guides light from one end to another end thereof and illuminates an object such as the inside of an organ of a human body while the inside of the organ is observed, all of which are installed in a flexible sheath of the electronic endoscope 1. The processing unit 2 includes therein an illumination device comprising an illumination lamp 8 such as a xenon lamp and lamp, energizing means 9 which energizes the illumination lamp 8 to provide illumination light rays, an iris 7 which is operated by an iris drive circuit 10 to limit the diameter of the bundle of light rays emanating from the illumination lamp 8 or close to shut off the illumination light rays, and a focusing lens 6 operative to focus the light rays passing through the iris 7 on a surface at one end of the light guide 3. The light rays emanating from the illumination lamp 8 and focused on the end surface of the light guide 3 are transmitted from the end surface to the other end surface of the light guide 3 and directed toward an object, such as the inside of an organ of a human body into which the electronic endoscope is inserted, to illuminate it. Light rays reflected by the object are focused on the solid state image pickup element 5 by the objective lens 6 so as to form an optical image of the object on the solid state image pickup element 5.

The processing unit 2 includes various circuits such as a vertical transfer signal interruption circuit 11, a drive signal generating circuit 12, a black balance adjusting circuit 13, a white balance adjusting circuit 14, a video signal processing circuit 15 and a display control circuit 16 therein. Specifically, the drive signal generating circuit 12 generates a drive signal with which the solid state image pickup element 5 is driven and controlled to photo-electrically convert the image thereon into image signals. The image signals provided by the solid state image pickup element 5 are adjusted in black and white balances by the black balance adjusting circuit 13 and the white balance adjusting circuit 14, respectively. The adjusted image signals are subsequently processed for gamma correction or control etc. by the video signal processing circuit 15 and then converted to television signals Sv by the display control circuit 16 and transmitted to a monitor television (not shown) to display an image of the object on the screen.

In the electronic endoscope system thus comprised, when a black balance adjustment command 18 is entered, the vertical transfer signal interruption circuit 11 actuated to interrupt vertical transfer pulses included in drive signals that are generated by the drive signal generating circuit 12 and admits horizontal transfer pulses included in the drive signals to the solid state image pickup element 5. Due to absence of vertical transfer pulses the solid state image pickup element 5 does not provide photoelectric transfer signals but transfers signals only through its horizontal transfer section. The black balance of the output signal from the solid-state image pickup element 5 is adjusted by the black balance adjusting circuit 13. After the adjustment of black balance of signals from the solid state image pickup element 5, the vertical transfer signal interruption circuit 11 removes the interruption of vertical transfer pulses with the result of admitting the drive signals from the drive signal generating circuit 12 left intact to the solid state image pickup element 5. Once the vertical transfer signal interruption circuit 11 removes the interruption of vertical transfer pulses, video signals provided in the form of photoelectric transfer signals by the solid-state image pickup element 5 are transmitted to the video signal processing circuit 15 where the video signals are subjected to gamma correction, etc. Subsequently, the video signals are converted to television signals Sv by the display control circuit 16. The processor 2 transmits the television signals to the monitor television to display an image of the object on the screen.

As described above in detail, the electronic endoscope system of the present invention has no necessity of controlling the quantity of light by the iris 7 when performing black balance adjustment of the electronic endoscope 1. Moreover, the electronic endoscope system of the present invention eliminates the provision of light shielding means for isolating the solid state image pickup element 7 from ambient light which is served for photoelectric transfer like as always necessary in the conventional electronic endoscope systems. As a result of the elimination of such a light shielding means, the electronic endoscope 1 is prevented from getting filthy due to contact with the light shielding means that is filthy and, in consequence, kept clean.

It is to be understood that although the present invention has been described with regard to preferred embodiments thereof, various other embodiments and variants may occur to those skilled in the art, which are within the scope and spirit of the invention, and such other embodiments and variants are intended to be covered by the following claims.

What is claimed is:

1. An electronic endoscope system comprising an electronic endoscope unit equipped with a photoelectric conversion element as an image pickup element for photoelectrically converting light from an object to electric signals and a signal processing unit for processing said electric signals to video signals, said processing unit comprising:

drive signal generating means for generating vertical and horizontal transfer signals as drive signals with which said photoelectric conversion element is driven;

color balance adjusting means for adjusting at least black balance of said photoelectric conversion element;

transfer signal interruption means for interrupting said vertical transfer signals from said photoelectric conversion element and admitting said horizontal transfer signals to the solid state image pickup element while said balance adjusting means is actuated.

2. An electronic endoscope system as defined in claim 1, wherein said color balance adjusting means comprises a black balance controlling circuit.

3. An electronic endoscope system as defined in claim 1, wherein said color balance adjusting means comprises a black balance controlling circuit and a white balance controlling circuit.

* * * * *